United States Patent [19]

Buono

[11] 4,057,499
[45] Nov. 8, 1977

[54] APPARATUS FOR SEPARATION OF BLOOD

[75] Inventor: Frank S. Buono, Garfield, N.J.

[73] Assignee: Becton, Dickinson and Company, East Rutherford, N.J.

[21] Appl. No.: 339,867

[22] Filed: Mar. 9, 1973

[51] Int. Cl. ............................................. B01d 33/00
[52] U.S. Cl. .......................... 210/136; 210/DIG. 23; 210/359, 210/516; 23/259
[58] Field of Search ................ 210/23, 136, 359, 416, 210/446, DIG. 23

[56] References Cited

U.S. PATENT DOCUMENTS

| | | | |
|---|---|---|---|
| 3,481,477 | 12/1969 | Farr | 210/359 |
| 3,586,064 | 6/1971 | Brown | 210/359 UX |
| 3,661,265 | 5/1972 | Greenspan | 210/359 |
| 3,693,804 | 9/1972 | Grover | 210/359 |
| 3,761,408 | 9/1973 | Lee | 210/23 |

Primary Examiner—Sidney Marantz
Attorney, Agent, or Firm—David S. Kane

[57] ABSTRACT

An apparatus for the separation and collection of plasma or serum from the cellular phase of a blood sample in a blood collection tube having a piston assembly provided with a cup shaped housing with a closed rear portion having a one-way valve extending therethrough with a filter disposed in the housing and formed with an open forward portion surrounded by a flexible peripheral flange of greater diameter than the internal diameter of the collection tube. The piston assembly can have a body member with a portion which permits the passage of the liquid phase and also has a peripheral projecting flexible flange of greater diameter than the internal diameter of the collection tube and having a smooth lower surface and a redially grooved upper surface so that when the piston assembly is shifted into the collection tube the lower surface of the flange has sealing wiping engagement with the inner wall of the container and the liquid phase will be forced through the central body portion of the piston assembly to be isolated on the other side thereof and so that when the piston is shifted outwardly the seal will be broken and the upper grooved surface of the flange engages the inner wall of the collection tube so that air can bypass through the grooves to the inner portion of the collection tube.

13 Claims, 6 Drawing Figures

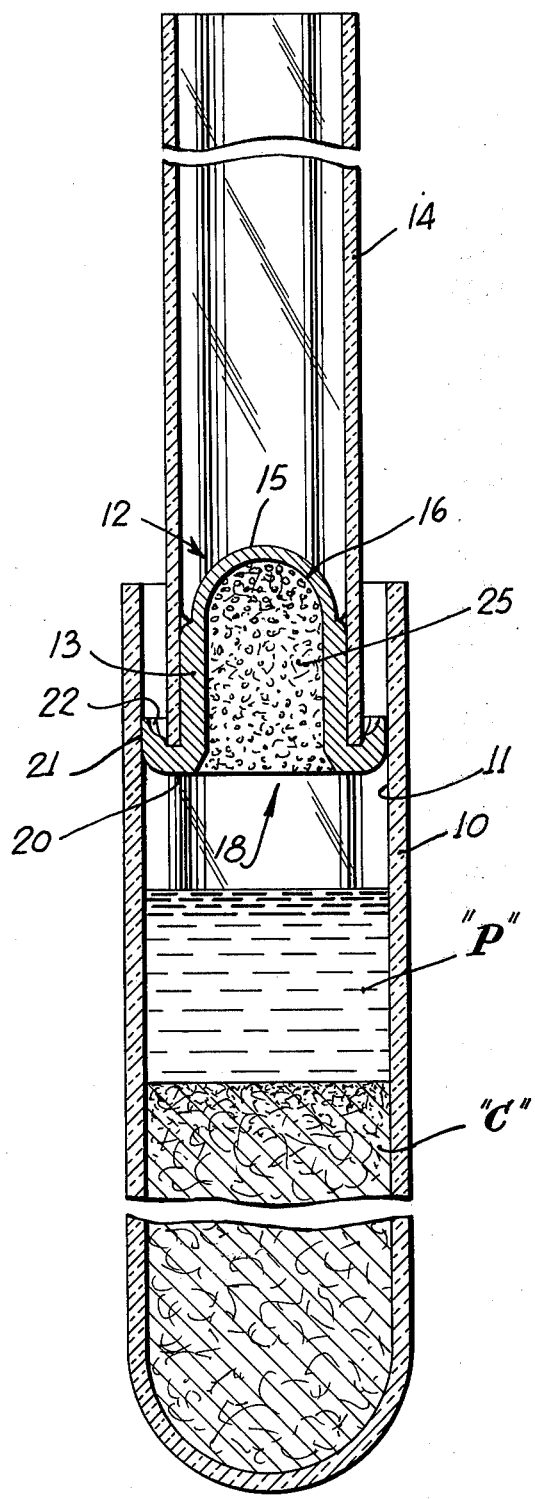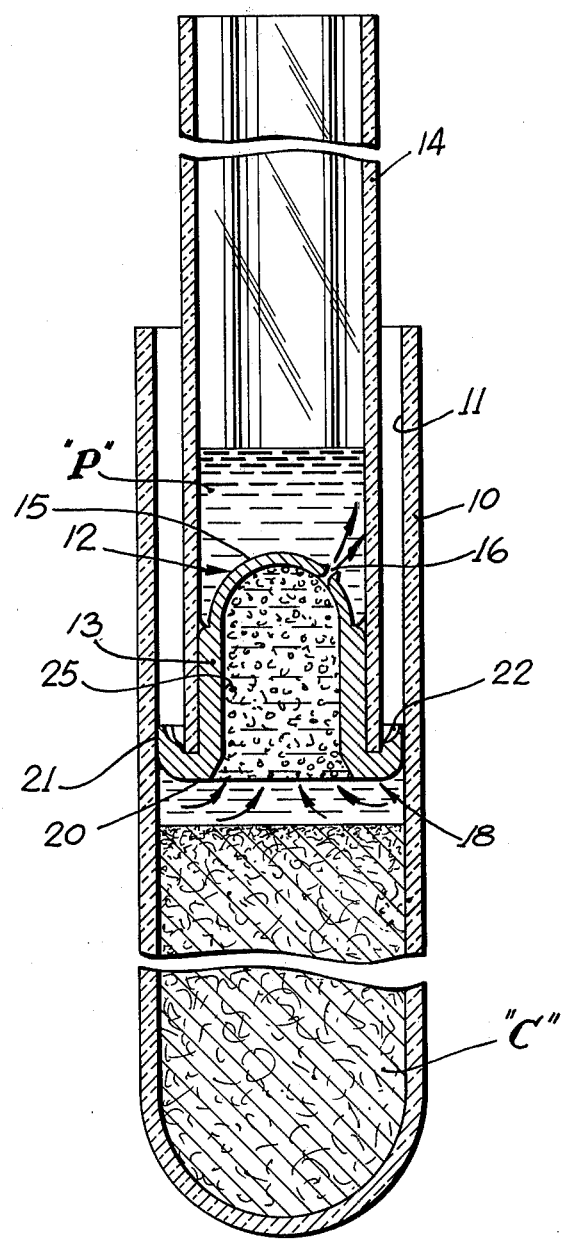

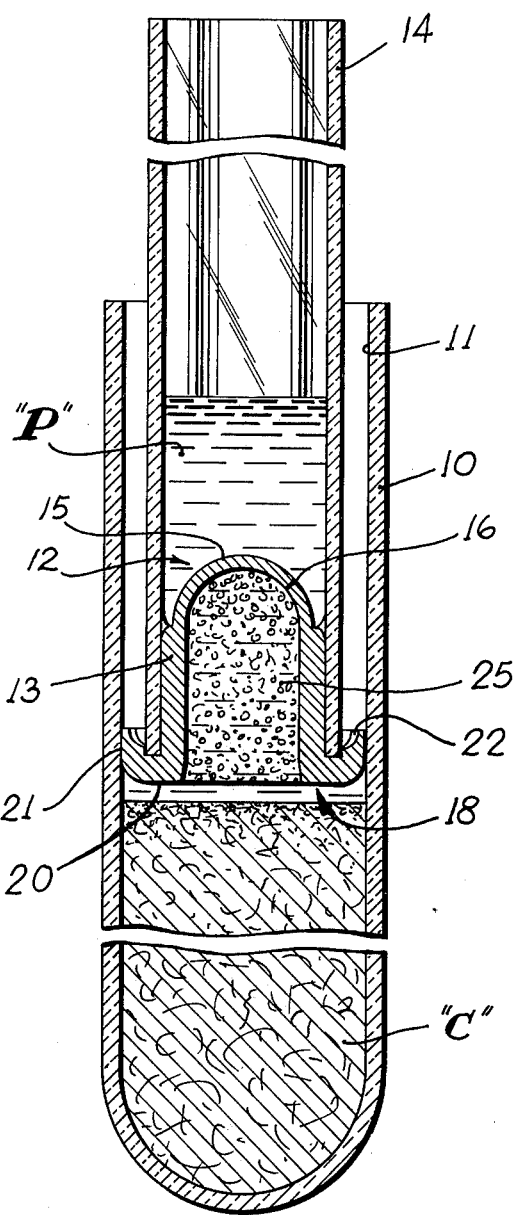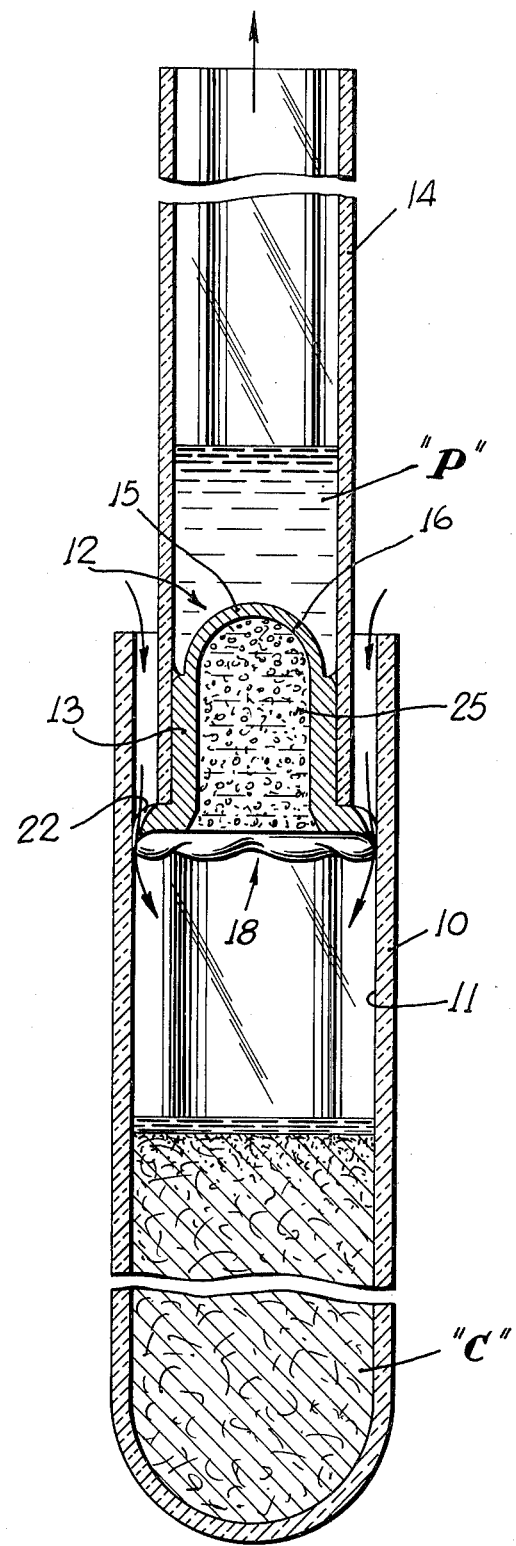

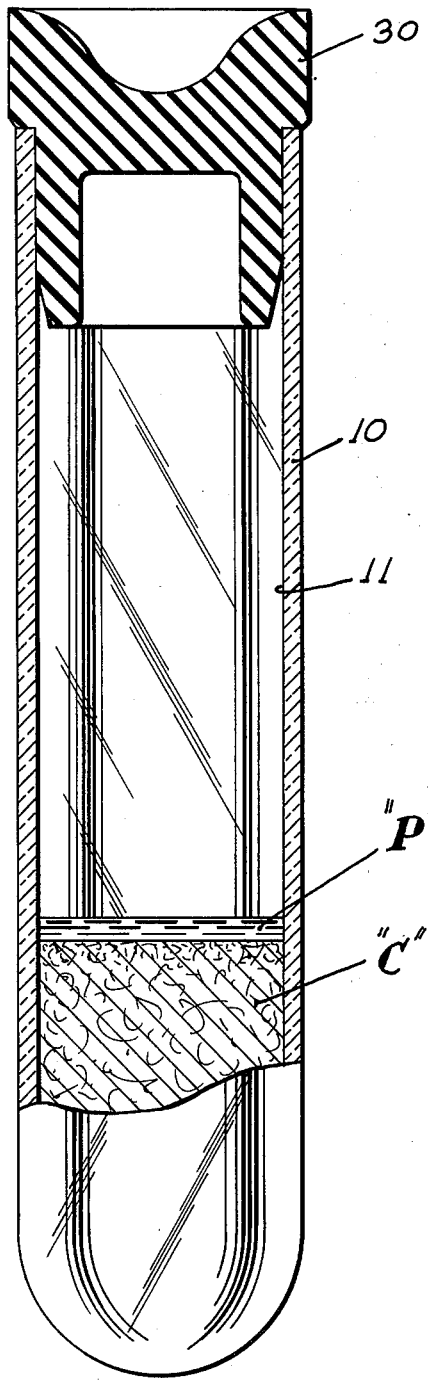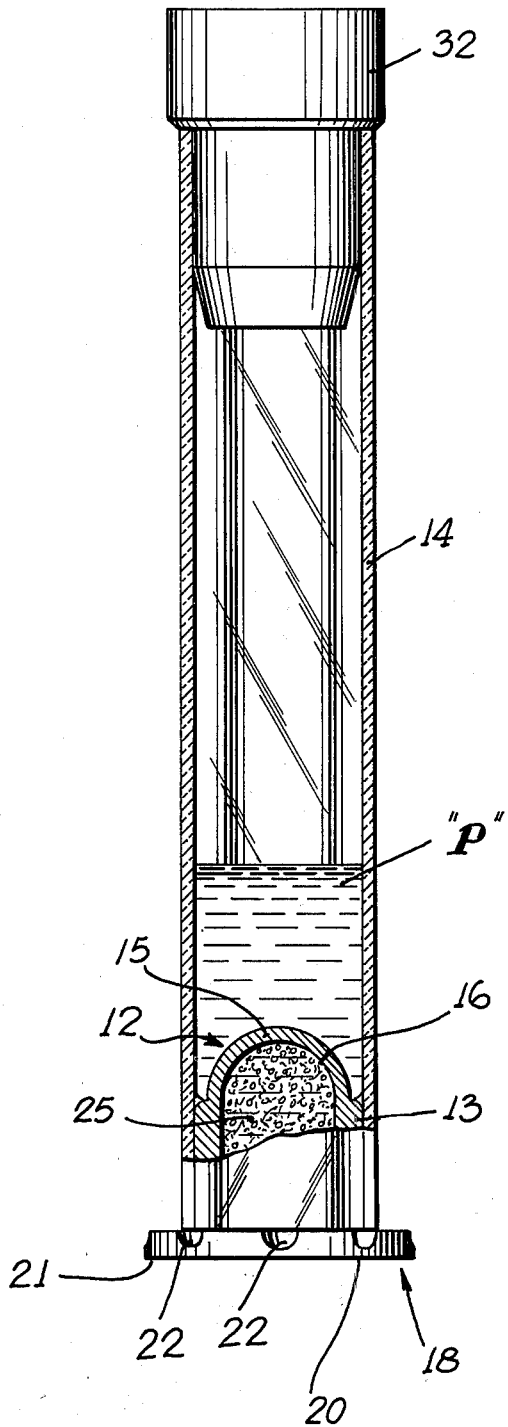

APPARATUS FOR SEPARATION OF BLOOD

BACKGROUND OF THE INVENTION

The present invention relates to an apparatus for separating blood into its component liquid plasma or serum phase and its solid cellular phase.

It is known that it is clinically desirable to isolate serum from clotted human blood as soon as possible after a blood sample has been collected and clotted. Serum that has not been isolated from the clot may undergo changes with certain chemical constituents rendering test data on those constituents misleading, for example, serum potassium, glucose and certain enzymes. Devices for the isolation or separation of the plasma or serum phase from the cellular phase of blood are presently employed. Several of these devices are disclosed in U.S. Pat. Nos. 3,355,098, 3,481,477, 3,508,653, 3,512,940, 3,661,265 and 3,693,804.

The present invention proposes to improve upon the separation and isolation of the solid and liquid phases of blood.

SUMMARY OF THE INVENTION

It is an object of the present invention to provide an improved piston assembly for use in apparatus for the separation and collection of plasma or serum from the cellular phase of a blood sample in which the piston includes a peripheral flange which forms sealing engagement with the interior wall of the collection tube as the piston shifts inwardly and which has an improved valve arrangement which automatically breaks the seal between the flange and the inner wall of the collection tube when the piston is shifted outwardly so that air can bypass the piston and enter into the inner end of the collection tube.

A further object is to provide in such apparatus an improved piston assembly in which a one-way valve and filter are arranged in tandem relationship so that the liquid phase passes through both the filter and valve as the filter is shifted inwardly in the collection tube and in which the filter is protected and encased in a housing integrally formed with the piston.

The objects of the invention are generally accomplished by providing a piston assembly for use in such apparatus having a projecting flexible peripheral flange of greater diameter than the internal diameter of the collection tube and having a smooth lower surface and a radially grooved upper surface so that when the piston assembly is shifted into the collection tube the lower surface of the flange has sealing engagement with the inner wall of the collection tube and when the piston assembly is shifted outwardly the upper grooved surface of the flange engages the inner wall of the collection tube whereby air can bypass around the piston assembly through the grooves. My invention also contemplates the provision of a piston assembly having a cup shaped filter housing with a closed rear portion having a one-way valve extending therethrough and having a filter disposed in and encased and protected by said housing and in engagement with the interior wall of the housing so that the liquid phase of the blood passes through both the filter and the valve as the piston assembly is shifted inwardly in the collection tube.

DESCRIPTION OF THE DRAWINGS

FIG. 1 is a sectional elevational view of my improved apparatus for the separation and collection of the liquid phase of blood showing the parts as they appear just prior to effecting separation.

FIG. 2 is a view similar to FIG. 1 except that the separating tube and piston assembly have been moved downwardly into the collection tube allowing the liquid to pass through the filter and valve into the separating tube.

FIG. 3 is a view similar to FIGS. 1 and 2 wherein the separating tube and piston assembly have moved downwardly into the collection tube to a position adjacent the solid-liquid interface showing the parts as they appear just prior to withdrawing the piston assembly and separating tube.

FIG. 4 is a view similar to the prior figures in which the separator tube and piston assembly is being removed from the collection tube with the bulk of the liquid phase separated from the heavy phase.

FIG. 5 is a sectional elevational view of the collection tube with the solid phase therein and showing it fitted with a conventional sealing stopper; and FIG. 6 is a sectional elevational view of the separator tube with the separated liquid phase therein and sealed at its lower end by the piston assembly and its upper end by a conventional sealing stopper thus being suitable for storing or shipment to a laboratory.

DETAILED DESCRIPTION OF THE PREFERRED EMBODIMENT

My improved apparatus generally comprises a blood collection tube 10, a separator tube 14 which may be telescopically inserted in the collection tube and a piston assembly 12.

The blood collection tube 10 is of a conventional construction being usually formed of glass or other material inert to blood, its components and reagents used therewith and is closed at its lower end and open at its upper end. The blood sample is collected therein in conventional manner and is suitably separated into its solid or cellular phase C and its liquid plasma or serum phase P.

The separator tube 14 is likewise made of suitable inert material such as glass or transparent inert plastic material and is preferably of uniform diameter throughout its length and open at both ends. The separator tube 14 is of suitable length to serve as an operating handle so that when the piston assembly 12 is shifted inwardly to the position shown in FIG. 3, in proximity to the interface between the liquid and cellular phases a portion of the separator tube will project above the collection tube to be readily grasped by the hand. The piston assembly 12 is preferably of unitary construction and is formed of material which is resilient, deformable and has flexible characteristics. It is also preferable that the material be elastic and be pierceable by a pointed blade. For this purpose natural and synthetic rubber and suitable plastic materials such as styrene butadiene serve very satisfactorily.

The piston assembly comprises generally a body portion 13 in the form of an inverted cup having a closed dome shaped inner end portion 15 and an open outer end portion provided with an integral outwardly projecting peripheral flexible flange 18 of greater diameter than the inner diameter of collection tube 10. The cup shaped portion serves as a filter housing for the filter 25 and it encases and protects the filter. The side walls of the housing are of cylindrical configuration and it is of slightly greater diameter than the inside diameter of the separator tube so as to have sealing fit therewith when inserted therein in the manner shown in the drawings with the lower end of the separator tube in engagement with the upper surface of the flange 18.

One or more one-way valves are formed in the dome shaped inner portion of the housing as shown at 16. These valves may take the form of a simple slit formed through the resilient elastic material. Due to the dome shaped configuration of this portion of the housing the valves will open when the piston is shifted inwardly in the collection tube through the liquid phase as shown in FIG. 2 and they will close when the inward shifting movement stops or when the piston assembly is shifted outwardly as shown in FIGS. 3 and 4 to thereby prevent the liquid phase from re-entering the collection tube.

The peripheral sealing flange 18 is provided with a smooth lower surface 20 and when the piston assembly is shifted inwardly in the collection tube as shown in FIGS. 1 and 2 the outer edge portions 21 of the smooth lower surface have wiping sealing engagement with the inner surface 11 of the collection tube 10 forcing the liquid phase upwardly through filter 25 and valves 16.

The sealing flange is also provided with an improved valve arrangement whereby air may bypass around the piston into the lower portion of the collection tube as the piston assembly is withdrawn. The improved valve arrangement comprises a plurality of radial grooves 22 formed in the upper surface of the flange 18. Thus, it will be seen that when the piston assembly is shifted outwardly in the collection tube 10 the grooved upper surface of the flange engages the inner wall 11 of the collection tube as shown in FIG. 4 and air can bypass the piston through the grooves 22 as indicated by the arrows. This permits ready withdrawal of the assembly when the liquid phase has been collected in the collection tube.

The filter 25 is employed to remove solid material such as fibrin from the liquid phase which may form after the cells have been separated from the serum. The filter may be made of any suitable material, inert to blood, its components and reagents, such as porous plastic material, for example, porous polyethylene, porous polyurethane, porous tetrafluoroethylene or from sintered glass, porous ceramic material or glass wool. The filter is encased in and protected by the housing and has engagement with the inner side wall thereof to prevent bypassing. Thus, there is a tandem relationship between the filter and one-way valve so that the liquid phase entering into the separator tube from the collection tube passes through both the filter and the valve.

In use, the filter is assembled as described in the cup shaped housing and this, in turn, is assembled in sealing relationship in the lower end of the separator tube. The blood sample is collected in the usual manner in collection tube 10 and after the liquid phase has been separated from the cellular phase as by centrifuging the end of the separator tube having the piston assembly is inserted through the open end of the collection tube in the manner shown in FIG. 1 and shifted downwardly through the liquid phase as shown in FIG. 2 to a position adjacent the interface between the two phases as shown in FIG. 3. As the assembly is shifted downwardly through the liquid phase the lower surface of the flange 18 forms sealing engagement with the inner surface 11 of the collection tube forcing the liquid phase upwardly through the filter 25 and the one-way valves 16 so that the liquid phase is collected in the separator tube. When the blood phases have thus been separated and isolated from each other the separator tube and piston assembly can then be withdrawn from the collection tube in the manner shown in FIG. 4. In withdrawing the piston assembly from the collection tube the upper surface of the flange 18 is then shifted into engagement with the inner wall 11 of the collection tube breaking the seal so that air can bypass around the assembly through the grooves 22 into the lower portion of the collection tube. Thus, the separator tube 14 with the liquid phase sample therein can be readily withdrawn from the collection tube. After the tubes have thus been separated a suitable sealing stopper 30 of conventional design can be inserted in the collection tube 10 and a suitable sealing stopper 32 may be inserted in the upper end of the separator tube 14. The lower end of the separator tube is sealed by the piston assembly 12.

The samples thus isolated from each other can be transported or shipped to a suitable laboratory for tests or can be stored for future use while thus sealed.

It will be noted that the several objects indicated at the beginning of this specification are thus accomplished by my improved apparatus. In addition, it will be noted that the liquid phase has been isolated from the cellular phase to prevent deleterios chemical interaction between the two. It will also be noted that the separator tube serves as a handle to shift the piston assembly and it also serves to stabilize it with respect to the collection tube as it is shifted with respect thereto.

It will be appreciated that various modifications may be made in the illustrated embodiment such as varying the arrangement of the separating means for supporting and shifting the piston assembly.

I claim:

1. A piston assembly for use in separating the liquid phase from the cellular phase of a blood sample in a blood collection tube of the type which is closed at one end and open at the other end which comprises:
    a central body member provided with a portion which permits the passage of the liquid phase and with a peripheral projecting flexible flange of greater diameter than the internal diameter of the collection tube and having a smooth lower surface and a radially grooved upper surface so that when the piston assembly is shifted inwardly into the collection tube the lower surface of the flange has sealing wiping engagement with the inner wall of the tube and the liquid phase will be forced through the central body portion to be isolated on the other side of the piston assembly and so that when the piston assembly is shifted outwardly the upper grooved surface of the flange engages the inner wall of the tube whereby air can bypass through the grooves to the inner portion of the collection tube.

2. A piston assembly as set forth in claim 1 in which the portion of the central body which permits the passage of the liquid phase comprises a one-way valve which opens when the piston assembly is shifted inwardly into the collection container through the liquid phase and closes when the inward shifting stops.

3. A piston assembly as set forth in claim 2 in which the piston assembly also includes a filter in tandem relationship with the one-way valve so that liquid passing through the valve must also pass through the filter.

4. A piston assembly for use in separating the liquid phase from the cellular phase of a blood sample in a blood collection tube of the type which is closed at one end and open at the other end which comprises:

a body provided with a cup shaped housing with a closed rear portion having a one-way valve extending therethrough and formed with an open forward portion surrounded by a peripheral flexible flange of greater diameter than the internal diameter of the collection container, said flange having a smooth lower surface and a radially grooved upper surface; and a filter disposed in and protected by said housing and in engagement with the interior wall of the housing so that liquid passing through the valve must pass through said filter.

5. A piston assembly as set forth in claim 4 in which the peripheral flange is provided with a smooth lower surface so as to form sealing wiping engagement with the interior wall of of the collection container as the piston assembly is shifted inwardly and with an upper surface provided with radial grooves so that when the piston assembly is shifted outwardly the upper surface will be in contact with the interior wall of the collection container and air can bypass through said grooves.

6. An apparatus for the separation of the liquid phase from the cellular phase of a blood sample comprising:

a blood collection tube open at one end and closed at the other end for collecting a sample of blood and for holding the blood while it is separated into liquid and cellular phases;

a separating tube open at both ends for receiving the separated liquid phase of smaller diameter than the collection tube so that it can be telescopically shifted therein;

a piston assembly for use in separating the liquid phase from the cellular phase comprising an inverted cup shaped body portion disposed in the end of the separating tube which is inserted in the collection tube in sealing engagement with the interior walls thereof and formed with a one-way valve extending through the inner portion thereof and with a peripheral flexible sealing flange extending around the outer portion thereof and projecting outwardly beyond the wall of the separator tube;

said flange being of greater diameter than the internal diameter of the collection tube and having a smooth lower surface so as to have wiping engagement with the inner walls of said collection tube when the piston assembly is shifted inwardly in the collection tube, and having a radially grooved upper surface so as to provide air channels between said flange and the inner walls of the collection tube when the piston assembly is shifted outwardly from said collection tube;

said valve being arranged to open when the separator tube and piston assembly are shifted inwardly through the liquid phase in the collection tube and to close when the shifting stops; and a filter disposed in said cup shaped housing and encased and protected thereby and arranged in engagement with the wall thereof so that liquid passing through said valve must pass through the filter.

7. An apparatus for the separation and collection of the liquid phase of a blood sample as set forth in claim 6 in which the peripheral flange has a smooth lower surface so that when the separating tube and piston assembly are shifted inwardly into the collection tube the lower surface forms sealing engagement with the inner wall of the collection tube and has an upper surface formed with radial grooves so that when the separator tube and piston assembly are shifted outwardly the upper surface is in engagement with the interior wall of the collection tube so that air can bypass through the grooves.

8. A piston assembly as set forth in claim 4 in which the closed rear portion of the housing is of concavo-concave dome shape and the valve comprises a slit formed therethrough.

9. A pressure differential filtering apparatus comprising:

an elongated sampling member having a hollow interior portion for the collection of liquid, one end of said sampling member having a resilient lip projecting radially outwardly to form a piston, said lip having a first surface for forming a seal with the interior walls of a container holding the liquid to be filtered and a second surface having a plurality of irregularities for breaking said seal with the interior walls of said container, said piston having a longitudinal passageway to allow liquid to pass therethrough into said hollow interior of said sampling member; and a porous filter member fitted within said longitudinal passageway.

10. The apparatus of claim 9 wherein said irregularities are in the form of serrations.

11. A pressure differential filtering apparatus for separating a liquid comprising:

a hollow cylindrical walled container having a closed bottom and an open top; an elongated sampling member having a hollow interior for the collection of liquid, one end portion of said sampling member having a resilient lip projecting radially to form a piston, said lip having a first surface for forming a seal with the interior walls of said container and a second surface having a plurality of irregularities for breaking said seal with the interior walls of said container, said piston having a longitudinal passageway to allow liquid to pass therethrough into the hollow interior of said sampling member; and a porous filter member fitted within said longitudinal passageway of said piston.

12. The apparatus of claim 11 wherein said irregularities are in the form of serrations.

13. An apparatus comprising a cylinder, and a piston capable of acting in cooperation with said cylinder, said piston having an elastomeric lip, said lip having a first surface forming a seal with the interior wall or walls of said cylinder when said piston is moved in one direction and a second surface engaging said wall or walls when said piston is moved in the opposite direction provided with a plurality of irregularities so that said second surface is incapable of forming a seal with the interior wall or walls of said cylinder.

* * * * *